United States Patent [19]

Schwab

[11] Patent Number: 4,551,073
[45] Date of Patent: Nov. 5, 1985

[54] PUMP FOR LIQUID AND GASEOUS FLUIDS, ESPECIALLY BLOOD

[76] Inventor: Walter Schwab, Kahlsperg 694, A-5411 Oberalm, Austria

[21] Appl. No.: 493,693

[22] Filed: May 11, 1983

[30] Foreign Application Priority Data

May 12, 1982 [AT] Austria ............................. 1857/82
Sep. 9, 1982 [AT] Austria ............................. 3364/82

[51] Int. Cl.⁴ .................... F04B 35/04; F04C 1/02
[52] U.S. Cl. ............................. 417/352; 417/410; 418/61 A
[58] Field of Search ............ 417/352, 353, 354, 410, 417/423 R; 418/54, 61 A

[56] References Cited

U.S. PATENT DOCUMENTS

| | | | |
|---|---|---|---|
| 2,772,046 | 11/1956 | Shomphe | 417/354 |
| 2,938,468 | 5/1960 | Kececiogln et al. | 417/410 |
| 3,221,664 | 12/1965 | Jernaes | |
| 3,268,156 | 8/1966 | Radziwill et al. | 418/61 A |
| 3,384,295 | 5/1968 | Hayner et al. | 417/354 |
| 3,913,408 | 10/1975 | Moore | 418/54 |
| 3,922,121 | 11/1975 | Garfinkle | 418/61 A |
| 4,118,157 | 10/1978 | Mayer | 418/54 |
| 4,296,500 | 10/1981 | Monties et al. | 418/61 A |
| 4,400,145 | 8/1983 | Hoffman | 418/61 A |

FOREIGN PATENT DOCUMENTS

| | | |
|---|---|---|
| 351137 | 10/1979 | Austria . |
| 355177 | 2/1980 | Austria . |
| 355704 | 3/1980 | Austria . |
| 2021513 | 11/1971 | Fed. Rep. of Germany . |
| 2242247 | 3/1974 | Fed. Rep. of Germany . |
| 2819851 | 11/1978 | Fed. Rep. of Germany . |
| 2250892 | 6/1975 | France . |
| 7504139 | 8/1975 | France . |

OTHER PUBLICATIONS

"Pulsatile flow blood pump based on the principle of the Wankel engine", by N. Verbiski et al., (from the Institute for Biomed. Eng., publ. Aug. 14, 1968, pp. 753-756.

"Einteilung der Rotations-Kolbemaschinen" by Felix Wankel, 1963 Deutsche Verlags Anstalt GmbH, pp. 7 and 22 & 23, plus 2 pages of dwg.

*Primary Examiner*—Cornelius J. Husar
*Assistant Examiner*—Peter M. Cuomo
*Attorney, Agent, or Firm*—Karl F. Ross; Herbert Dubno

[57] ABSTRACT

A rotary pump has a trochoidal member and a trochoidal rotary piston which preferably forms a gap seal with the trochoidal surface of the housing so that damage to blood cells and the like is avoided when the pump is used as an artificial heart or to assist circulation. The rotor is jounaled on an eccentric within a housing which may be the casing of an electric motor for driving the pump. The motor and its speed reducer, preferably planetary gearing, are disposed wholly within the rotor.

20 Claims, 16 Drawing Figures

PUMP FOR LIQUID AND GASEOUS FLUIDS, ESPECIALLY BLOOD

CROSS REFERENCE TO RELATED APPLICATION

This application is related to my concurrently filed copending application Ser. No. 493,694.

FIELD OF THE INVENTION

My present invention relates to a pump for gaseous and liquid fluids, especially biological suspensions and most particularly blood. The invention thus relates to a pump which can be used in blood circulation for clinical purposes and which has sufficiently small dimensions and spatial requirements for its throughput to enable it to be used, as well as an artificial heart as as one of the pumping elements of an artificial heart.

In general terms therefore, the invention relates to a rotary pump and especially an electric powered rotary pump of trochoid chamber configuration, operable with emulsions and suspensions such as blood, with pumping frequencies of up to 200 revolutions per minute (rpm) while applying minimum stress to the material which is pumped, thereby eliminating possible damage to cellular structures in this material.

The blood pump of the invention, being capable of displacing such emulsions and suspensions and especially biological fluids in the oxygenating or peripheral circulation of the human patient or an animal, can be used to assist in such circulations or to provide the sole motive power for either or both of the circulations.

BACKGROUND OF THE INVENTION

Generally in the efforts hitherto made to provide an artificial heart or a pump capable of displacing blood and adapted to be implanted in the patient, a pneumatic or hydraulic drive for the displacement membrane was provided. Such devices require a massive support structure located outside the body and delivering energy to the membrane via the pneumatic or hydraulic fluid.

Consequently, efforts have been expanded in developing rotary pumps which can serve this purpose. In the discussion below, I will touch on some of the earlier pumps of this type provided for the displacement of blood or as artificial hearts or as circulation-assisting implanted pumps. I will also touch other rotary means, not specifically developed for use with blood which have structural similarity to the heart pump of this invention.

For example, the basic structure of the invention includes a pump chamber having a wall which is formed as a single lobe or two-lobe trochoid, respectively, in a 2:3 or 1:2 ratio with a rotor which has three corners or edges or two corners or edges, respectively, running along the trochoidal wall of the chamber and driven by an eccentric. These means are known for vastly different purposes, including so-called Wankel machines and are not suitable for use as heart pumps. The ratio referred to is the ratio between full revolutions of the motor to full revolutions of the driving eccentric.

For example, as described in the aforementioned copending application, when a single lobe chamber and the two-corner rotor device is used in a 1:2 ratio pump, the contact between the corners and the trochoidal wall can cause serious damage to the red blood corpuscles which are sheared between the wall and the rotor, thereby releasing hemoglobin and inducing premature heraolysis, which can be detrimental to a patient.

Trochoidal means with rotary pistons are described, for example in U.S. Pat. No. 3,221,664, in French patent No. 2,250,892, in French patent No. 2,260,008, in British patent No. 1,350,728, in German patent document DE-OS No. 2,021,513 and in Austrian Pat. No. 355,704, No. 355,177 and No. 351,137.

Not one of these references describes or suggests an effective electrically powered pump which can be utilized as an artificial heart or heart pump.

It is, therefore, interesting to note that most of the art dealing with artificial hearts or heart pumps has concentrate on membrane pumps whereby the force transmission between the pressure plate and the membrane is effected by a pneumatic or hydraulic fluid even if a pressure plate is electromechanically displaced.

However, in German patent document DE-OS No. 28 19 851, which is equivalent to French Pat. No. 2,389,382 and U.S. Pat. No. 4,296,500, a rotary pump using a trochoid rotary piston principle is described. This pump is generally similar in structure to the pump described in the publication "Einteilung der Rotationskolbenmaschinen" by F. Wankel. To the extent that this pump can be utilized as an artificial heart it is driven by an electric motor outside the pump housing and many of the disadvantages of the other trochoidal rotary piston means described above are present here as well.

Mention may also be made of the publication "Pulsatile Flow Blow Pump based on the Principle of the Wankel Engine" by N. Verbiski et al. in the *Journal of Thoracic and Cardiovascular Surgery*, volume 57, No. 5, May 1969, pages 753–756, describing a 2:3 Wankel machine.

It is known to operate a membrane pump for the displacement of blood with an electromagnetic solenoid as well. The disadvantage of this arrangement, however, is that its size does not generally permit convenient implantation if it is to have sufficient blood displacement capacity. If the pump has a sufficiently small size to permit implantation, its capacity is insufficient.

OBJECTS OF THE INVENTION

It is, therefore, the principal object of the present invention to provide a pump for gases and liquids which is free from the disadvantages enumerated above and which, in principle, combines small-size with high capacity and excellent reliability.

Another object of this invention is to provide a pump which is capable of being implanted to assist natural body circulation or to substitute for the heart of a patient, i.e. to constitute an artificial heart which has its drive and rotary pumping member self-contained and which is of generally simple and reliable construction.

Yet another object of this invention is to provide an improved electric motor-driven blood pump for the purposes described which is less detrimental to the cellular components of the blood than earlier pumps.

SUMMARY OF THE INVENTION

These objects and others which will become apparent hereinafter are attained, in accordance with the invention, in a pump for the purposes described which comprises a pump chamber formed with a trochoidal wall and especially the wall of a single-lobe or double-lobe trochoid, a rotor (rotary piston) rotatable in this chamber and driven by an eccentric drive to displace the fluid from at least one inlet port to at least one outlet port, the rotor having a trochoidal configuration with two "corners" or "edges" in the case of a single-lobe trochoidal chamber surface or three "corners" or "edges" in the case of a trochoidal chamber surface of bilobar type, and a small, high-speed electric motor with low torque output disposed at least in part in the interior of the rotary piston and provided with a transmission coupled to the eccentric drive fro delivering the lower speed and higher torque necessary to rotate the rotor.

According to the invention, the transmission and the electrical parts of the motor are provided within the rotary piston centrally in an axial position and the transmission is a planetary drive. The electric motor can have a housing portion which forms the eccentric and a hollow shaft projecting axially only from one side of the eccentric motor, the eccentric shaft being eccentric also with respect to the motor axis while the eccentric drive can comprise one or more eccentric gears, discs or wheels which are disposed laterally in the piston.

According to a feature of the invention, two eccentric motors can be used for operating a double-sided planetary gear transmission disposed centrally of the rotary piston in the axial sense thereof with each electric motor having its housing fixed to forming part of the eccentric and each electric motor having only a single axially extending hollow shaft which is eccentric to the motor axis.

The invention thus provides a pump construction utilizing principles of trochoidal machines but of an extremely compact configuration enabling the pumps to be used as implanted pumps and as artificial heart pumps.

According to another feature of the invention, the rotary piston in a 2:3 ratio slip contact three-corner piston configuration (triangular or trilobar configuration) has a planetary gear transmission with two uniformly distributed planetary gear units. The same can apply to a 1:2 two-corner piston rotating in a single-lobe chamber. In both cases, the load is preferably distributed via two or three transmission branches, the transmission can be made extremely compact and the entire motor can have relatively small dimensions.

This construction of the planetary gear transmission permits within the rotary piston a counterrotation between the rotating parts which can include the motor housing, the piston itself or parts of the transmission so that the desired ratio can be obtained for rotation of the piston in the slip contact type of pump for the particular trochoidal path desired. Instead of a two-stage planetary transmission, a three-stage transmission can be utilized to further reduce the speed and increase the torque delivery and, of course, it is also possible although less preferred to use a single-stage planetary grear transmission.

The electric motor which can be used, can be any conventional electric motor of the high-speed low-torque type, namely, in alternating current or a direct current motor with or without brushes or commutators.

According to another feature of the invention, the electric connection to the or to each motor is effected through an electric terminal or plug contact formed within the stationary planetary shaft of the assembly or unit.

When the pump is used as a blood or heart pump of the 1:2 ratio type, the intake and discharge ports (see the aforemetnioned copending application) can be formed as peripheral or lateral ports (see also German patent document DE-OS No. 22 42 247 and Austrian Pat. No. 355,177, respectively, describing a rotary piston pump and a compressor).

When the intake and outlet openings are peripheral ports, it is advantageous to provide them so that, in the dead-point position of the piston, the two pump compartments have maximum and minimum values respectively, with the intake and discharge ports in the dead-point position of the piston lying directly opposite the piston corners or edges whereby the piston via its corners or edges automatically blocks and unblocks these ports so that separate values detrimental to the blood can be avoided.

When the intake port is provided along the periphery and the discharge port is a lateral opening or the lateral port is a lateral opening and the discharge port is a peripheral opening, a backflow in the dead-point position of the piston is achieved by providing the lateral port so that in the dead-point position of the piston it is covered by the leading and trailing piston edges or flanks.

The intake and discharge ports can also be provided exclusively as lateral openings so that, in the dead-point position of the piston, both of the lateral ports are within the region enclosed by the leading and trailing flanks of the piston. This permits pressure equalization within the pump whose chambers are sealed off from the ports.

According to still another feature of the invention, especially when the pump is to be used as a heart pump, a minimum damage to red blood cells is desired, the sealing corners or edges of the piston lobes do not resiliently bear against the trochoidal surface of the chamber but rather are set back slightly from the latter by a constant distance to form a so-called gap seal with the housing. A gap seal is a spacing between the sealing members, one of which is fixed and another of which is movable, whereby a gap is maintained between the two members with a width of the order of a micron so that under the pressure differentials which are generated, practically no flow occurs across the gap and yet red blood cells are not sheared between the movable member and the stationary member.

In this construction, corners of the lobes of the piston, which are to form the gap seal with the housing, have radiuses which are slightly less than a equidistant between the trochoid surface generated by the corner and the surface of the housing spaced by the equidistant from the aforementioned trochoid.

The lateral walls define with the juxtaposed flanks of the rotor a constant-width gap of the order of a micron.

Thus a contactless construction can be formed by the piston in the housing. Where some contact is desired, adjacent the regions of contact, a gap seal is provided in the manner previously described.

To form an artificial heart from a single-lobe chamber and a 1:2 ratio piston having two corners, two such pumps can be coupled together in a single unit or body to imitate the functions of the two ventricles and the respective atria of the natural heart, one pump serving the pulmonary circulation while the other serves the peripheral circulation.

When the artificial heart is to be constituted from the 2:3 pump, which should also have the contactless or substantially contactless seals previously described, a two-lobe chamber is provided which has two opposite points in a continuous contact with the three-lobe piston or rotor so as to define two pumping chambers each of which has an intake and a discharge port and each of which serves as a respective pump for one of the two circulations.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
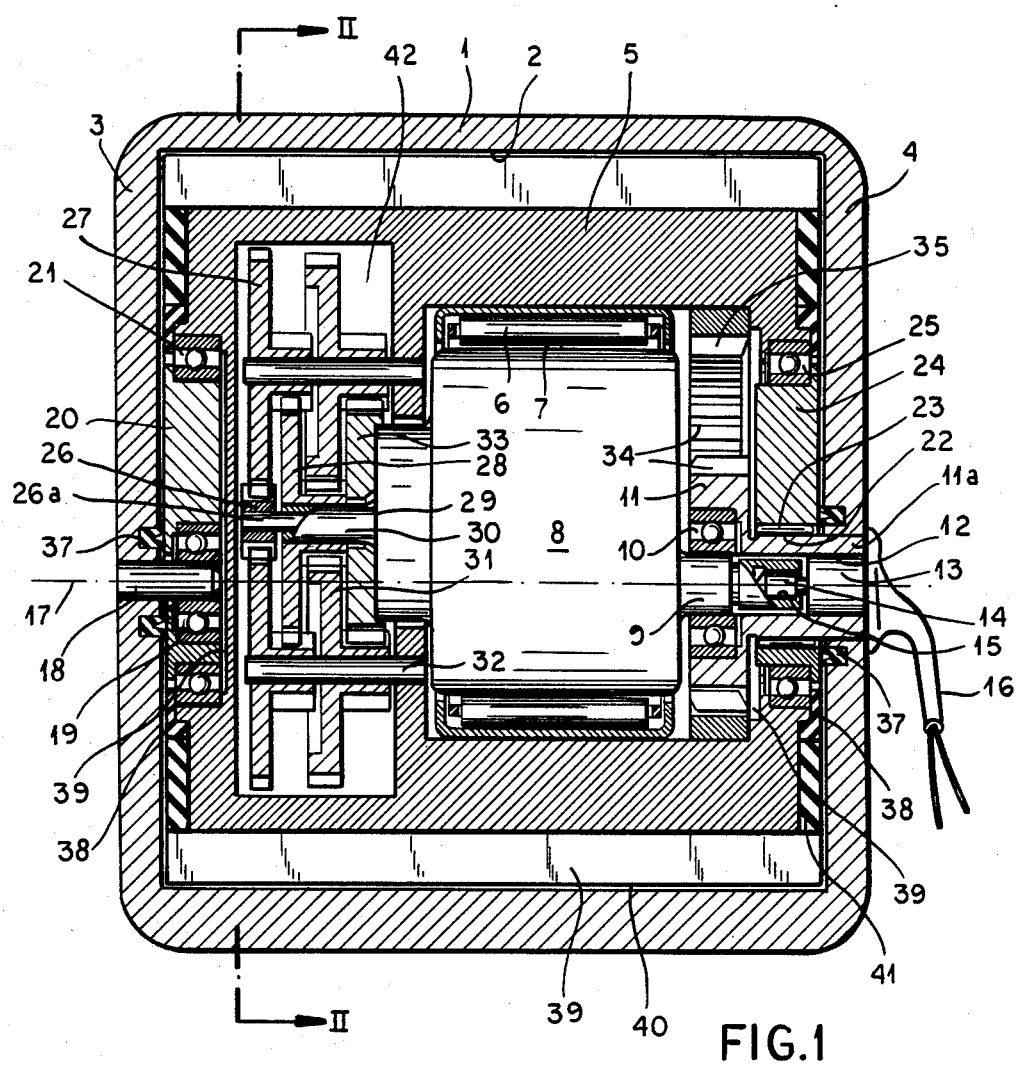
FIG. 1 is an axial cross-sectional view taken along line I—I of FIG. 2 and showing a trochoidal rotary piston pump with a 2:3 ratio and a generally triangular or trilobar piston and a bilobar chamber in accordance with the invention.
Figure 2:
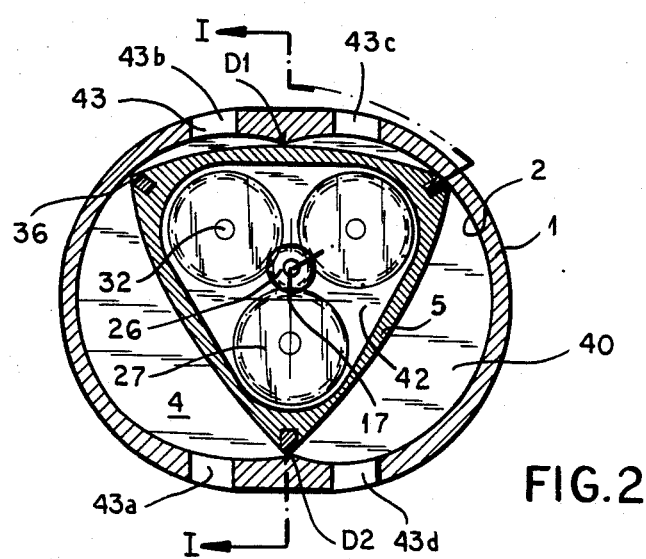
FIG. 2 is a radial section taken along the line II—II of FIG. 1.

In FIGS. 1 and 2, I have shown a heart pump utilizing a pump housing 1 having a trochoidal wall 2 of its pumping chamber 40 which constitutes a two-lobe trochoid disposed between side walls 3 and 4, the side wall 3 being invisible in FIG. 2.

The housing receives a generally triangular piston 5 journaled at 6 on a housing 7 forming an eccentric an constituting part of an electric motor 8 whose eccentric shaft is represented at 9 and is journaled at only one side of this eccentric motor via a bearing 10 in a hollow shaft which can be formed with a gear wheel 11.

This hollow shaft extends through the side wall 4 and provides an internal bore 11 which receives an electrical connector 13 forming a plug whereby electrical conductors 16, supplying the motor are delivered via the contacts 14 of this plug to the wiper contacts 15 of the motor. These wiper contacts are connected in the usual manner to the windings of the motor (not shown).

Since the eccentric shaft 9 projects from the motor only at one side and is supported through the bearing 10 via the hollow shaft 11 on only one of the side walls 4, it is important to define the eccentric axis 17 at the other side wall 3 as well.

To this end, a journaling pin 18, fixed in the side wall 3, is provided with a bearing 19 journaled in an eccentric disc 20 with the same eccentricity as the eccentric 7 and supporting, via a bearing 21, the left-hand end of the rotary path 5.

Correspondingly, at the side of the eccentric shaft 9, a bearing 23 is provided on a bearing seat 22 formed directly upon the projection 11a of the hollow shaft and carries an eccentric disc 24 which can have the identical outer diameter of the eccentric disc 20 and which is also journaled by a bearing 25 to radially support the right-hand end of the piston 5.

This construction ensures that, in spite of the fact that the eccentric shaft does not extend axially through the rotatable piston, no axial tilting moment can develop.

The speed of the pump is, of course, dependent upon the speed (rpm) of the electric motor suitably stepped down by planetary gearing.

The driving element of this gearing is a sun gear 26 which is driven by the motor, as opposed to the shaft 9 which is fixed to the eccentric housing 7. To this end, the motor shaft 26a can project out of a sleeve 30 rigid with a lateral portion 29 of the motor.

The sun gear 26 keyed to the shaft 26a meshes with three angularly equispaced planet gears 27 which are rotatably mounted on shafts 32 fixed to the piston 5 which thus serves as a planet carrier. The speed reduction can be enchanced by using multiple stage gearing and, to this end, a sun wheel assembly 28 is journaled on the hollow shaft 30 and meshes with a second set of planetary gearing 31 carried by the planet shafts 32 of the planet carrier or piston 5.

The planetary gears of the second stage speed reduction unit 31 meshes with the sun gear 33 fixed on the side wall 29 of the electric motor thereby creating from the eccentric housing 7 a driven sun-gear shaft such that the housing 7 and the piston 5 are rotated in opposite senses. These oppositely rotating members can also be coupled together by an output gearing which can include a ring gear 35 of the transmission 34. The ring gear 35 is fixed to the rotating piston 5 and meshes with the externally toothed hollow gear 11 previously described.

The piston 5 is trilobar and has at its corners or sealing edges sealing bars 36 which, in the embodiment shown, are in a continuous but light contact with the trochoidal surface 2 of the housing. As will be apparent hereinafter, it is also possible and indeed preferred to form these corners or edges so that gap seals are provided which are substantially out of contact with but parallel to the trochoidal surface 2 to minimize damage to the red blood cells.

Seals 37 recessed in the side walls 3 and 4 and sealing rings 38 recessed in the piston 5 seal the interior 39 of the piston against these walls of the housing with respect to the eccentric discs 20 and 24.

Additional sealing rings 41 of a flat configuration can also be provided around the periphery of the piston along the opposite end faces thereof to additionally seal the pump chamber 40. Thus the entire planetary gear transmission 42 can be fully enclosed within the interior of the piston 5 together with the electric motor.

Figure 8:
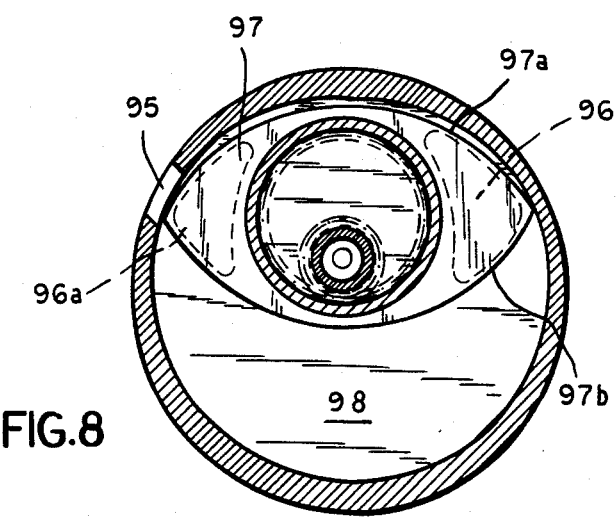
FIG. 8 is a view similar to FIG. 7 illustrating another embodiment with respect to the orientation of the ports.

Intaking discharge ports represented generally at 43 and specifically at 43a through 43d can be provided in the peripheral wall 2 of the housing or can be replaced by lateral ports in the side walls 3 and 4 as described, for example, in connection with FIG. 8.

The embodiment of FIGS. 1 and 2 can be modified by providing a gear equivalent to the hollow gear 11 on the pin 18 and by providing the gear 35 on the left side of piston 5 to mesh with the gear carried by the pin 18.

Thus, when the electric motor is driven with a speed reduction and torque multiplication afforded by the planetary gear transmission, the motor housing and the piston are rotated in opposite senses and consequently, the piston orbits along its epicyclic path to displace the fluid from the intake port to the discharge portin circulating the blood.

Figure 3:
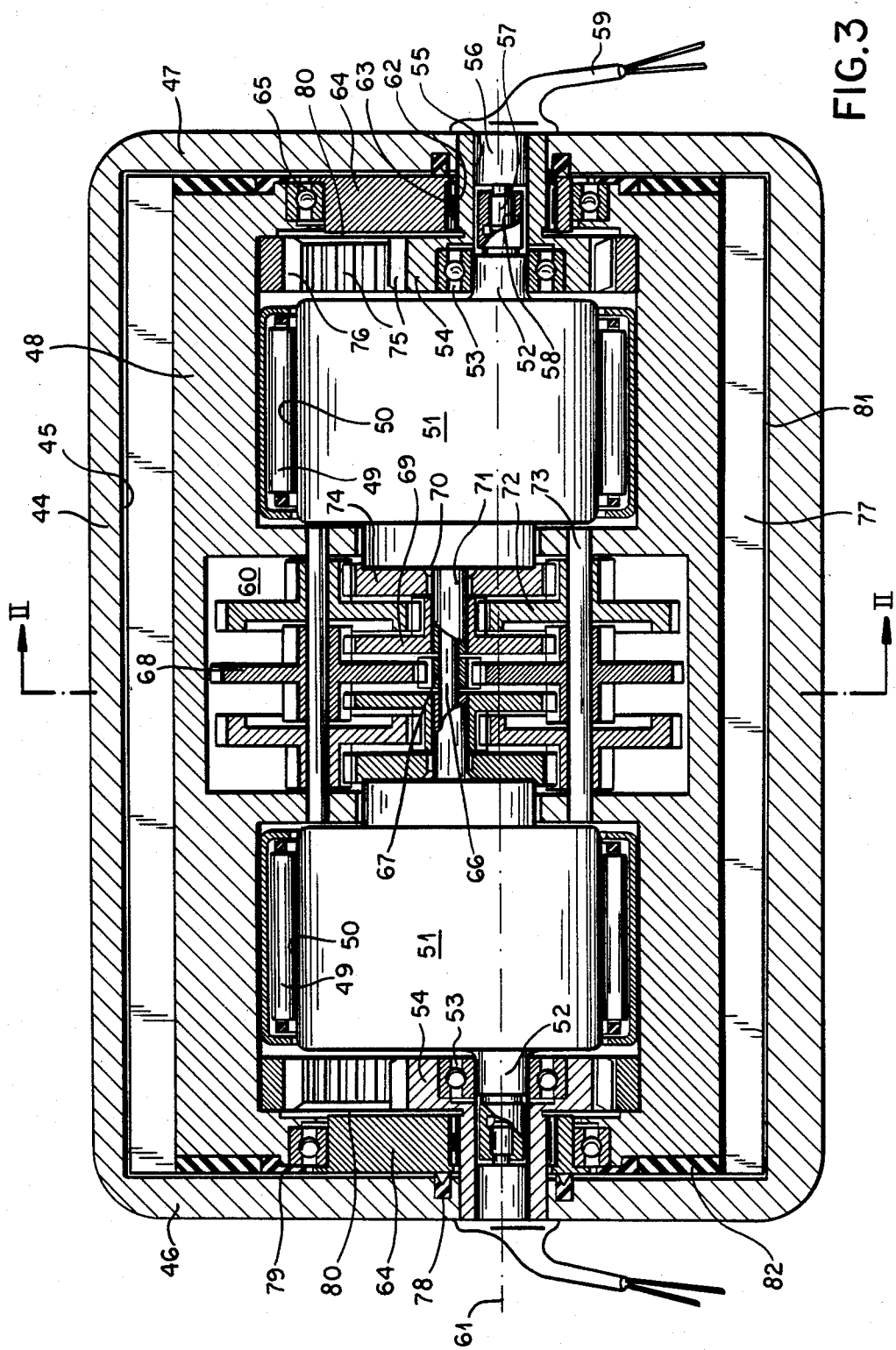
FIG. 3 is a view similar to FIG. 1 of a pump having two electric motors and a triangular piston as described in connection with FIG. 1 in a 2:3 trochoid rotary piston pump for blood dispersements.

In the embodiment of FIG. 3, where two electric motors are used, each of the electric motors can be of an especially small size because both contribute to the final torque which is delivered to the rotary piston 48. This embodiment can have a cross section similar to that shown at FIG. 2 and is provided with a single planetary gear transmission which is of the multistage type for the two electric motors.

More particularly, the pump of FIG. 3 comprises a housing 44 having the trochoidal surface 45 disposed between two side bars 46 and 47 to define the pump chamber.

The trilobar piston 48 is journaled on respective bearings 49. Upon the housings 50 are two motors 51 disposed symmetrically on opposite sides of a vertical median plate through the axis of a shaft 66 which will be described in greater detail subsequently.

Here, each of the motor housings 50, is formed with a respective eccentric shaft 52 fixed, thereon and extenting only from one side of the housing but supporting the motor via a bearing 53 in a hollow gear shaft 54 whose hollow portion extends through the respective side wall to form a socket 55 for a plug 56 whose contacts 57 engage the wiper of slip ring contacts 58 of the respective electric motor to supply the electric motor with electric energy from the conductors 59.

Here again, a throughgoing electric shaft is not provided. Consequently, the planetary gearing 60 must be supported on the common rotor shaft 66 which is exposed between stubs 71 fixed to the confronting housing portion 70 of the two motors 51.

By having the hollow shaft 54 which traverses the side wall 46 for one motor and the side wall 47 for the other motor precisely coaxial along the theoretically electric shaft axis 61, tilting moments can be avoided.

Each of the hollow shafts 54 also is formed with a respective bearing surface 62 rotatably supporting a respective disc 64 which, in turn, radially supports the respective end of the rotor 48 by a bearing 65, the disc 64 here being identical to one another.

The speed of the pump is determined by the speeds of the two motors or, more accurately, by the speed of the common motor shaft 66.

The planetary transmission 60 comprises a sun gear 67 keyed to the shaft 66 and a planet gear set 68 for this sun gear. Beach of the planet gear of this set is carried by a respective shaft 73 corresponding to the layout of the planet shafts in FIG. 2, the shaft 73 being fixed to the rotor 48 which thus serves as a planet carrier.

The planet gears mesh with respective sun gears each of which is rotatable on a respective fixed stub 71 on the housing 50 and has a pinion meshing in turn with another planet gear 72 which a respective second size of planet gears on the shafts 73. These latter planetary gears mesh with sun gears 74 fixed to the housing 50 in the manner previously described so that each housing forms a respective sun gear wheel of the transmission. The rotor 48 is thus driven in a direction opposite that of the housing 50. The motion of the rotor 48 is defined by respective ring gears 76 fixed to the rotor 48 and eccentric with respect to but meshing with the hollow gears 54 previously described.

While the output transmission 75 thus far has been shown to have two parts disposed symmetrically to the outside of each motor 51, it is possible in reducing the length of the motor to provide only a single such output gear. Seals 78 recessed in the side walls 46 and 47 and seal 79 recessed in the end faces of the rotary piston 48, seal the interior 80 of the rotary path against the pump chamber 81. Sealing strips 77 are provided on the corners of the lobes in the manner already described, if desired, or else a gap seal as is preferred can be provided. The end faces may also be sealed by members 82. The entire planetary transmission 60 is, of course, enclosed in the interior of the piston and the intake and discharge ports can be provided as shown at 43 in the periphery or lateral walls of the housing.

As can be seen from FIG. 2, the planet shafts 32 or 73 are angularly equispaced by 120° from one another about the axis of the piston 5 or 48. A similar arrangement is provided for the planet shafts for a trilobar piston.

Figure 7:
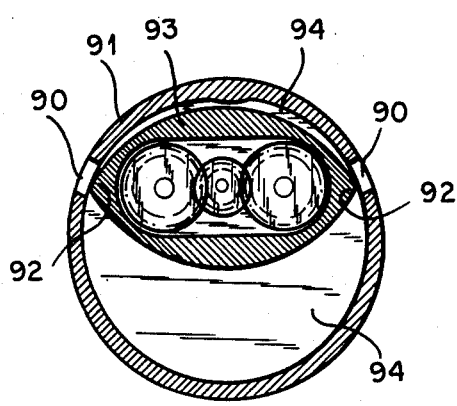
FIG. 7 is a radial section through a 1:2 ratio trochoidal rotary piston pump with its two-corner piston in the dead-point position.

When, however, a rotary pump of a 1:2 ratio and only two sealing corners or edges in a single-lobe chamber is provided in a slip system of the type described, all of the features hitherto illustrated and described in FIGS. 1–3 remain except that only two planet shafts are provided on the piston for the planet gearing and these are set opposite on another with 180° offset about the center of the piston (see FIGS. 7 and 8). Naturally, this latter modification will also apply for a two-lobe system.

For a 1:2 transmission of the type represented by the planetary gearing 60 but especially for a 2:3 ratio transmission, the driven sun gears 74, which in the embodiment of FIG. 3 are externally toothed gears, can be formed as internally toothed gears and mounted in the inner chamber of the piston 48 and fixed to the latter. In this case, the piston 48 is constituted as the driven sun gear shaft while the planet shafts 73 can be affixed to the electric motors 51 and the latter thus constitute the planet carrier.

This has been found to provide, for a minimum length of the pump, a comparatively large transmission ratio. Another advantage of this latter construction is that the electric shaft does not have to be interrupted by the planetary transmission 60 since the tow inner parts 70 of the electric motors can be rigidly connected by the planet shafts 73 so that aunitary structure is provided between the members 52 and opposite sides of the pump.

For calculating the precise contours of the piston and the chamber, reference may be had to the article "Kreiskolbenmotoren des Systems NSU-Wankel—ihre Berechnung und Auslegung", Fachzeitschrift Technica No. 8, 1973, Birkhäuser Verlag, Basel, Switzerland and the publication "Rotationskolben-Verbrennungsmotoren" by W. D. Bensinger, 1973, Springer Verlag, Berlin-New York-Heidelberg.

Figure 4:
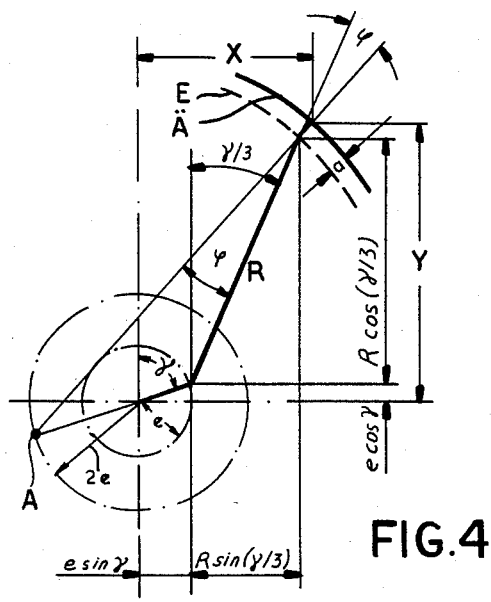
FIG. 4 is a geometric diagram explaining the equidistant between the epitrochloid generated by rotation of the rotor and the trochoidal surface of the housing for the purpose of explaining the gap seal of the invention.

In FIG. 4, I have illustrated the geometric relationships which are applicable in defining the equidistant which is used, in turn to provide a gap seal in the manner described in the aforementioned copending application. This illustration applies to a two-lobe and an analogous single-lobe trochoidal surface of the housing with respect to which sealing is effected.

The equation defining a two-lobe epitrochoid is:

$$x = e \cdot \sin\gamma + R \cdot \sin\frac{\gamma}{3}, y = e \cdot \cos\gamma + R \cdot \cos\frac{\gamma}{3}. \quad (1)$$

A sealing bar whose running surface precisely follows the epitrochoid must have a tip or point. To provide a sealing surface of constant width, the epitrochoid E must be increased by a small constant distance a which is referred to herein as the equidistant to the epitrochoid E and which defines the enlarged trochoidal path Ä which represents the housing surface. The trochoidal path Ä is thus defined by the equations $$x = e \cdot \sin\gamma + R \cdot \sin\frac{\gamma}{3} + a \cdot \sin\left(\frac{\gamma}{3} + \phi\right), \quad (2)$$

$$y = e \cdot \cos\gamma + R \cdot \cos\frac{\gamma}{3} + a \cdot \cos\left(\frac{\gamma}{3} + \phi\right).$$

These equations include the traverse of swing angle $\phi$ which is the angle between the generating radius and the normal path. The angle $\phi$ is defined by the relationship $$\phi = \arccos\frac{R + 3e \cdot \cos\frac{2}{3}\gamma}{\sqrt{R^2 + 9e^2 + 6R \cdot e \cdot \cos\frac{2}{3}\gamma}}, \quad (3)$$

$\phi$ max is achieved when angle A is a right angle:

$$\sin\phi_{max} = \frac{3e}{R}. \quad (4)$$

For a single-lobe trochoidal surface the equations or the trochoid enchanced by the equidistant a is defined by the equations $$x = e \cdot \sin\gamma + R \cdot \sin\frac{\gamma}{2} + a \cdot \sin\left(\frac{\gamma}{2} + \phi\right), \quad (5)$$

$$y = e \cdot \cos\gamma + R \cdot \cos\frac{\gamma}{2} + a \cdot \cos\left(\frac{\gamma}{2} + \phi\right).$$

The equations for the traverse angle $\phi$ in this case are given by:

$$\phi = \arccos\frac{R + 2e \cdot \cos\frac{\gamma}{2}}{\sqrt{R^2 + 4e^2 + 4R \cdot e \cdot \cos\frac{\gamma}{2}}} \quad (6)$$

$$\sin\phi_{max} = \frac{2e}{R}. \quad (7)$$

Figure 5:
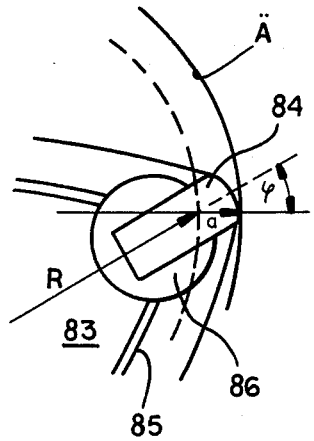
FIG. 5 is a detail view of a corner of a piston in a construction analogous to that of a Wankel engine.

FIG. 5 shows a corner or sealing edge of a piston 83 whose sealing bar 84 in the conventional way has a radius equal substantially to the equidistant a hereinafter referred to as the equidistant radius. This bar 84 thus is in continuous contact with the surface Ä.

However, as previously noted such continuous contact is not desirable and hence, although not readily visible in FIGS. 1 through 3 and the FIGS. subsequently to be described because of this problem of scale, I prefer to maintain a very slight gap in the micron range between the sealing bar and the surface.

Figure 6:
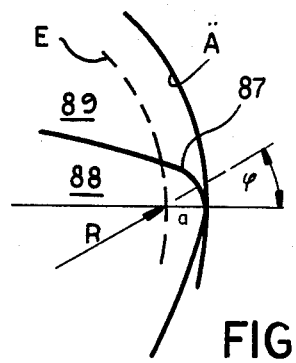
FIG. 6 is a detail view of the corner of a piston for use as a blood and heart pump according to the invention.

To this end, as shown in FIG. 6, the corner or edge 88 of the piston will have a circular curvature 87 at least over the angle $\phi$ which is of a radius r<a where a is the equivalent radius. The center of curvature of this circular arc is the intersection between the epitrochoid and the radius r and is the point from which the equidistant radius a is measured. (a−r) should therefore be a value of the order of a micron. I have found that with a gap seal of this type premature hemolysis does not occur and destruction of the cells is a minimum. The gap, because of its small size, is not visible in FIG. 6 but will be understood to be present.

FIGS. 7 and 8 have been illustrated for a 1:2 ratio single-lobe trochoid housing and two-corner piston for use as a heart pump. As can be seen from FIG. 7, intake and discharge ports 90 can be provided in the peripheral wall 91 of the housing in the form of elongated orifices. When the piston 93 is in its dead-point position as shown, these orifices lie directly opposite the corners 92 and the pump chambers 94 have maximum and minimum volumes. This construction has been found to eliminate the need for separate valves in the heart pump applications. It will be obvious that any additional structures in the nature of such valves may create problem sites because of agglomeration of cells, or may create problems by introducing additional elements which may break down.

Another preferred arrangement of the ports has been shown in FIG. 8 wherein a peripheral port 95 is provided in the peripheral wall of the housing while another port 96 is provided laterally in the side wall 98. In this case, in the dead-point position of the piston 97, the port 95 lies opposite one corner of the piston while the port 96 is covered by the flanks 97a and 97b of the other corner of the piston. Naturally, instead of a peripharl port 95 another port 96a can be provided laterally.

The openings 96 and 96a may be provided mirror symmetrically in the same lateral wall or may be provided mirror symmetrically in pairs of both of the lateral walls or even in a nonsymmetrical relationship whereby one intake port is provided in one of the lateral walls while the other port is provided in the other lateral wall.

As is also apparent from FIGS. 7 and 8, to increase the throughput and to avoid physiologically detrimental suction at the intake ports, each intake port can have a larger cross section in the respective discharge port. Other variations of the structures described are also possible as may be required for use of the device in a heart pump. For example, one peripheral inlet can be associated with two lateral outlets, two lateral inlets may be associated with one lateral outlet, two lateral inlets can be associated with a peripheral outlet, etc.

Figure 9:
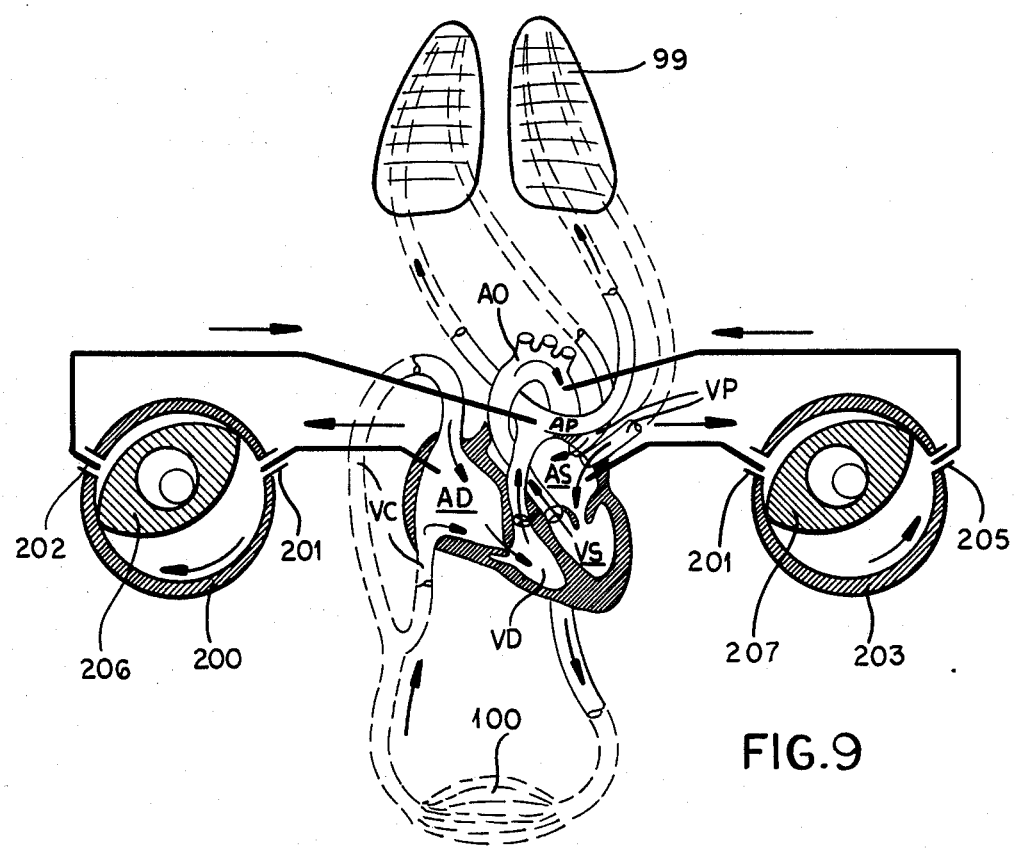
FIG. 9 is a diagram showing the application of two pumps of the type illustrated in FIGS. 1 and 7 as implanted pumps for assisting the natural circulation in a patient.

Referring to FIG. 9 it can be seen that two of the 1:2 ratio pumps of the type shown in FIG. 7, for example, can be utilized to support or assist in the circulation of a patient.

For example, the pump shown at 200 to the left of FIG. 9 can have an intake port 201 connected to the right atrium AD into which the inferior and superior vena cavae VC empty from the peripheral circulation which is represented at 100.

The outlet 202 of this pump opens into the pulmonary arteries AP supplying the blood to be oxygenated to the lungs 99.

The enous return VP from the lungs is, of course, delivered to the left atrium AS and is admitted to the left ventricle to be displaced through the oarta AO to the peripheral circulation 100. The natural contractions of the heart also displace blood from the right atrium AD to the right verticle VD from whence this blood is delivered to the pulmonary arteries AP.

The peripheral circulation is assisted by another similar pump 203 whose intake port 204 is connected to the left atrium AS and whose discharge port 205 opens into the aorta AO.

Naturally, the two pumps can be coupled together so that the rotors 206 and 207 thereof displace precisely the same volumes per unit time through the pulmonary and peripheral circulations.

Figures 10, 11, 12:
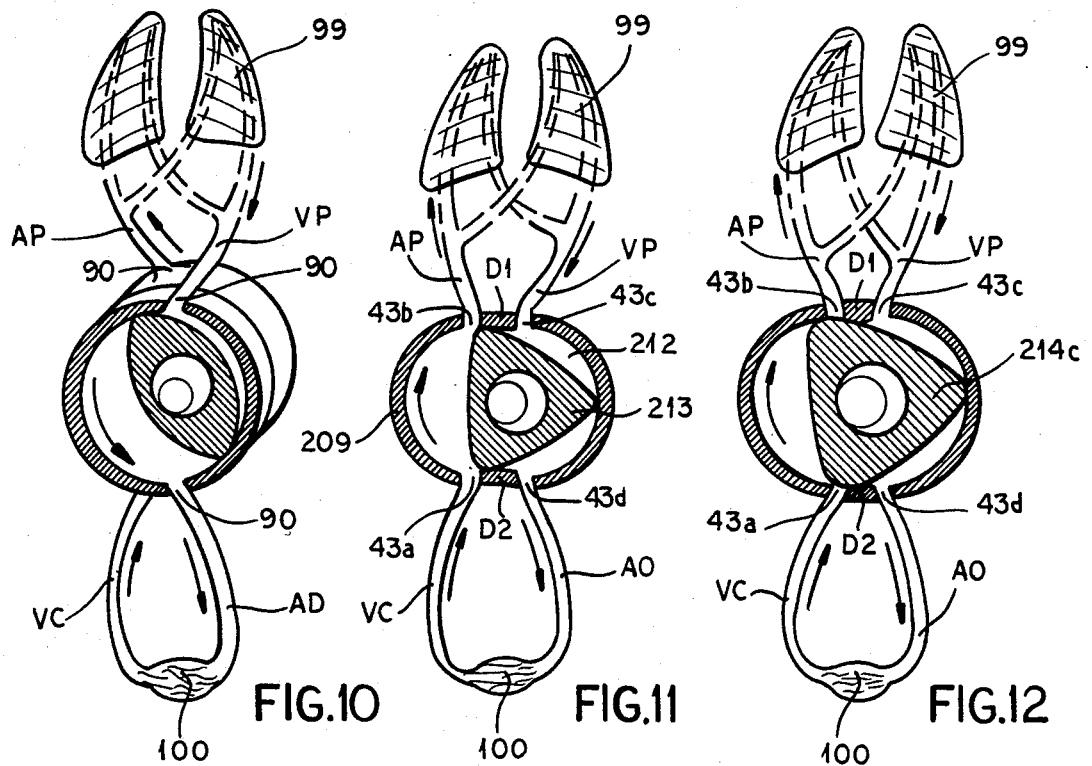
FIG. 10 illustrates the use of two such pumps as a total heart replacement.
FIG. 11 is a diagram circular to FIG. 10 but showing the heart pump with the triangular piston serving as the artificial heart.
FIG. 12 is a view similar to FIG. 11 in which a trilobar piston is used which has a hypotrochoidal cross section.

In FIG. 10 I have shown two similar pumps ganged together and serving as an artificial heart as distinct from the circulation and assist function of FIG. 9. Here the outlet of one pump supplies the pulmonary arteries AP while its inlet is connected to both vena cavae VC of the peripheral circulation 100. The inlet of the other pump receives the venous return from the pulmonary veins VP and delivers the oxygenated blood via its outlet at the aorta AO of the pulmonary circulation. The ports have all been represented at 90 in this figure.

The two pumps can be formed in a single body to facilitate implantation and the two chambers can have equal volumes and trochoids in the walls with spaces supported perpendicular to the generatrices so that each space receives a respective piston and each piston can be driven as described in connection with FIGS. 1–3 by one or two electric motors.

In FIG. 11 I have shown a generally triangular piston whose corners are rounded in accordance with the principles described in connection with FIG. 6 to form gap seals and whose surface is continuously contacted by a pair of oppositely disposed regions D1 and D2 of the two-lobe inner wall to seal two chambers 209 and 210 from one another respectively. These chambers represent the right and left parts of the heart pump when the unit is connected with its ports 43 in an artificial heart or heart replacement mode. For example, the venous return from the peripheral circulation 100 is here applied to the chamber 109 via a port 43a and the blood to be oxygenated is delivered to the pulmonary arteries AP for supply to the lungs 99 via port 43b.

The venous return from the lungs is delivered by the pulmonary veins VP to the port 42c of chamber 212 and is pumped into the aorta AO through the port 43d as the piston 213 is electrically driven as described in connection with FIGS. 1 through 3.

In the embodiment of FIG. 12, I have shown another artificial heart utilizing a pump in a ration of 2:3 but with a trilobar piston 214.

Figure 13:
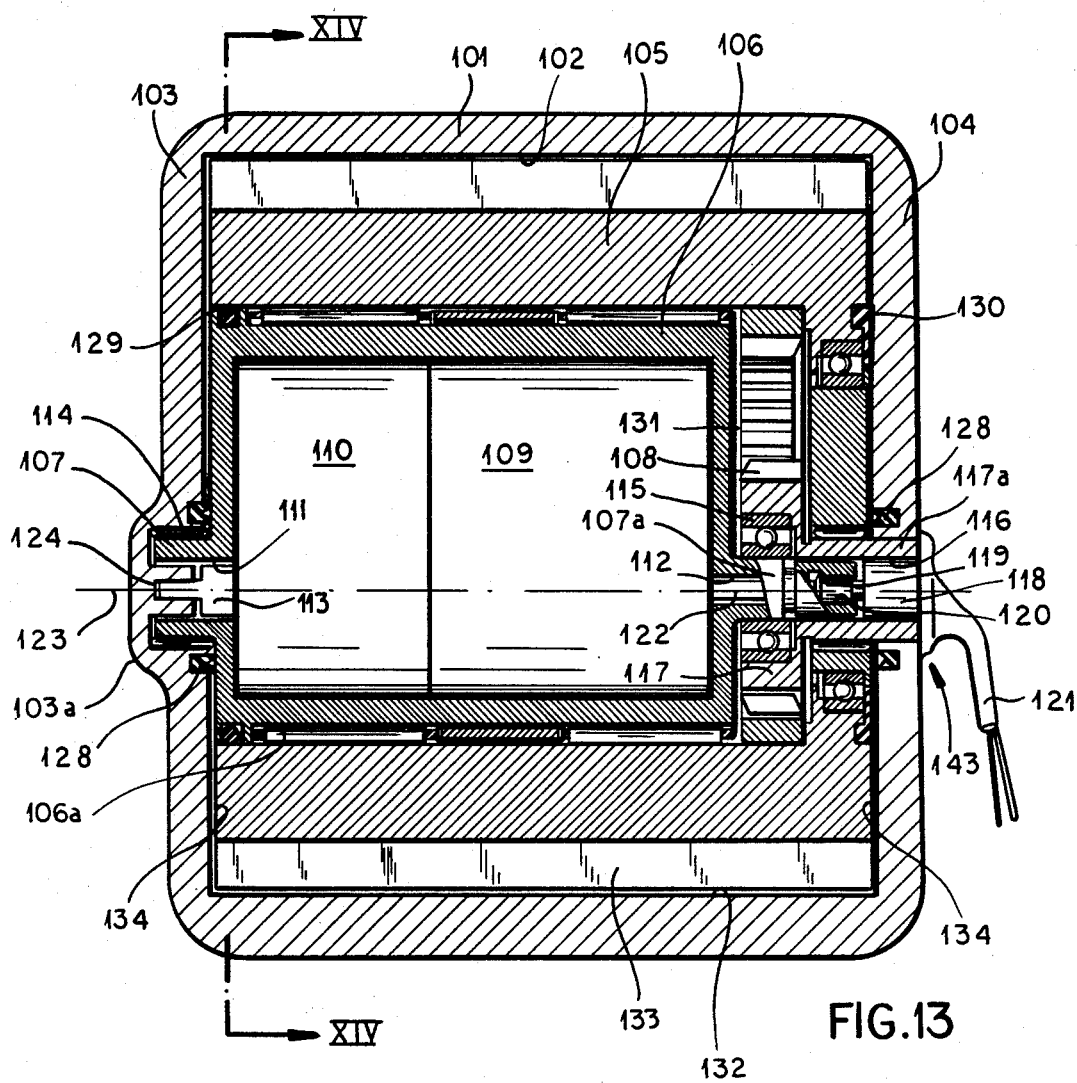
FIG. 13 is an axial section through a heart pump illustrating another embodiment of the invention taken generally along the line XIII—XIII of FIG. 14.

In FIGS. 13 though 16 I have shown a rotary pump having a housing 101 formed with the trochoidal inner surface 102 which defines the pumping chamber with a pair of lateral walls 103 and 104. The wall 103 is not visible in FIGS. 14 and 16.

Within the housing, a generally triangular piston 103 is eccentrically driven and, to this end, is mounted on an eccentric 106 whose eccentric shaft 107 is journaled by a bearing 114 in the lateral wall 103 which can be provided with a boss 103a for this purpose. This eccentric shaft 107 defines an eccentric axis 123 and the eccentric 106 is supported at its opposite side by a similar stub 107a which is received in a bearing 115 in a hollow gear 117 of a gear transmission represented at 108. The hollow gear 117 has a shaft 117a which is lodged in the opposite lateral wall 104 of the housing.

The movement of the piston 105 is controlled by the gearing 108 so that the corners or edges of the piston, which can be provided with sealing bars 133, form gap seals with the wall 102 in a preferred embodiment of the invention and as described but may, if necessary, slidingly contact this wall.

The drive unit comprises an electric motor 109 within the eccentric 106 which is mounted by needle bearings 106a within the piston 105 so that it can rotate independently of the piston.

The electric motor 109 is provided with a speed reduction transmission 110 which lies axially adjacent the motor 109 and is not shown in any detail, both the motor 109 and its speed reducer 110 being disposed within the eccentric 106 and secured thereto.

The eccentric shaft stubs 107 and 107a are formed with respective bores 111 and 112. The bore 111 is traversed by the drive shaft of the transmission 113 while the bore 112 is traversed by the electrical connector to the motor winding as will be described.

The hollow gear 117 has a bore 116 into which a plug 118 of the current supply conductors 121 can be connected. This plug 118 has currents 119 which engage wiper contacts 120 connected to the motor via the conductor 122 running through the bore 112.

Figure 14:
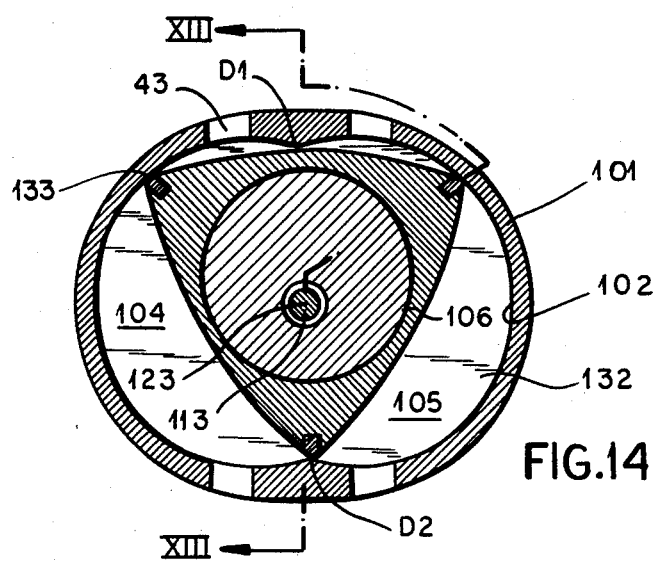
FIG. 14 is a radial section taken along the line XIV—XIV of FIG. 13.

In FIGS. 13 and 14, the driven transmission shaft 113, which is coaxial with the theoretical exterior axis 123, extends into the wall 103 and has noncircular plug connection 124 therewith whereby this shaft is held against rotation relative to the housing. Since the eccentric shaft is nonrotatable with respect to the housing, the piston must rotate and, by engagement via its internal gear 131 with the hollow gear 117, generate the trochoid movement within the pump housing.

Figure 15:
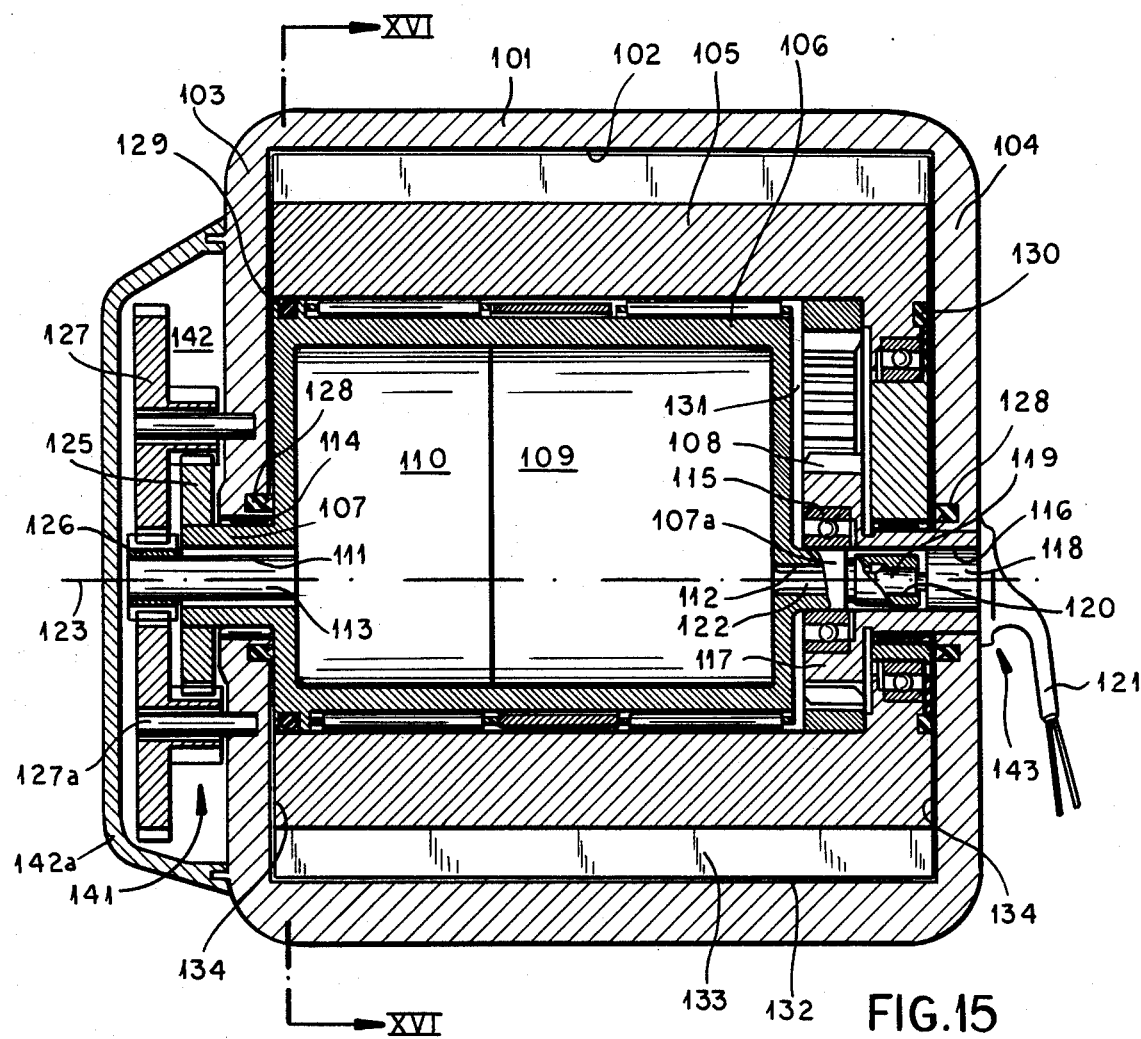
FIG. 15 is a view similar to FIG. 13 but in a section along the line XV—XV of FIG. 16.
Figure 16:
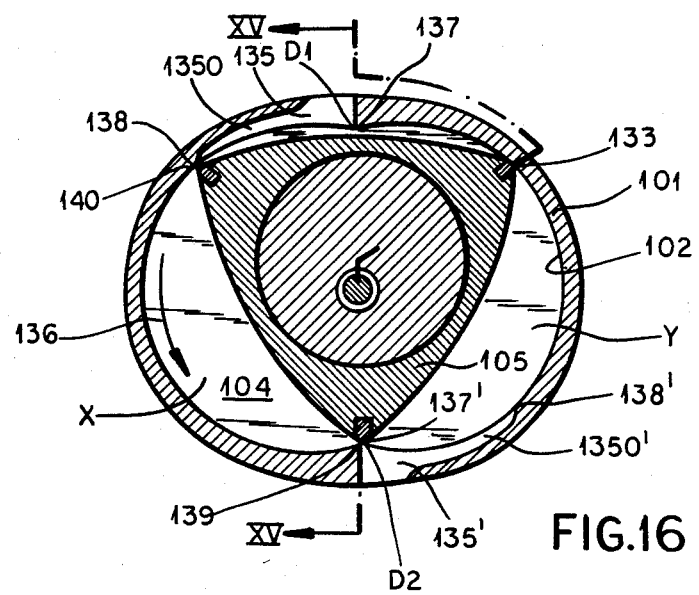
FIG. 16 is a section along the line XVI—XVI of FIG. 15.

The FIGS. 15 and 16, the eccentric shaft 107 projects through the housing wall 103 and is connected on the opposite side thereof with a sun gear 125 which meshes with three planetary gears 127, only two of which are visible and which are mounted on shafts 127a angularly equispaced about the eccentric axis 123. These planet gears 127 mesh, in turn, with a sun gear 126 connected to the output shaft 113 of the transmission. The shafts 127a are fixed on the housing 101 so that the latter acts as a stationary planet carrier for the speed-reducing gearing 125–127. This gearing 141 is received in a chamber 142 enclosed in a cam 142a mounted on the housing 101.

The gearing 141, driven by the speed reducer 110, thus rotates the eccentric shaft 107.

In another deviation from the embodiments described in connection with FIGS. 13 through 16, the driven shaft 113, which of course can be provided on the opposite side of the housing in the region of wall 104, can be operatively connected to the transmission 108 while the plug connection for energizing the motor can be on the housing wall 103.

Analogously, the embodiment of FIGS. 13 and 14 have a bore 116 for the plug 118 but can receive a connection 124 at the wall 104 for connecting the drive shaft with the housing while the connector arrangement 118–121 is provided at the housing wall 103.

A similar construction can be provided in the embodiment of FIGS. 15 and 16 as well.

In both embodiments seals 128 recessed in the lateral walls 103 and 104 can seal the eccentric with respect to the housing. The eccentric 106 can have seals 129 recessed therein and/or seals 130 can be recessed in the piston to seal off the pumping member 132. Radial seals in the form of bars 133 can be provided if there is contact between the piston and the trochoical wall. Seals 134 disposed on the lateral faces of the piston can complete the sealing means as may be necessary.

FIG. 16 also shows that the peripheral housing wall can be formed with intake and discharge ports 135 and 135' which open at the trochoidal surface 102 and each of which can have an overflow pocket 1350 or 1350' which can be formed as a recess in the surface 102. The positions and dimensions of the ports 135 and 135' with their respective pockets 1350 and 1350' are so selected that, when viewed in a radial section and considered in the direction 136 in which the piston 105 rotates, the control edges 137 and 137' at the upstream side of each port coincide with the contact points $D_1$ and $D_2$ of the two-lobe trochoid of the surface 102, that in the dead-point position of the piston 105 the chamber X ahead of the pocket 1350 is at its maximum volume, chamber Y communicating with the pocket 1350' is at its maximum volume and the third chamber is at its minimum volume, that in this position one of the corners 140 of the piston coincides with the down stream edge 138 while another corner coincides with the edge 137', and that the third corner reaches the upstream edge 137 when the second corner of the piston reaches the edge 137' of the pocket 1350'.

This arrangement has been found to be particularly effective for a valveless pump for generating pressure and suction with only a unidirectionally rotatable piston for the displacement of gas or fluid to, for example, a membrane blood pump or the like.

Since the pump power for a pump of the invention when utilized as a heart pump can be 3 to 9 watts depending upon the volume to be displaced and the rate of displacement, it is advantageous to form the transmission 141 with a plurality of stages for greater speed-down ratios and to provide a larger electric motor within the eccentric 106. In this case, the speed reducer can be eliminated. When the outer wall of the electric motor forms the eccentric itself, the motor is in closer proximity to the blood which can act as a heat exchange medium to remove thermal energy from the pump.

The chamber 142 of the transmission 141 and the entire electrical installation 143 generally will be sealed completely against the surrounding organs and, of course, the electric system will include means for protecting the system against leakage or fault currents.

I claim:

1. A pump for gas or liquid fluids, especially blood, comprising:
   a housing having a peripheral wall formed with a trochoidal surface having at least one lobe;
   a rotor formed as a rotary piston body in said housing having at least two edges defining respective seals with said surface;
   an eccentric in said rotor and rotatable relative thereto define a trochoidal movement for said rotor edges along said surface whereby said fluid is displaced by said rotor;
   an inlet port and an outlet port formed in said housing for delivering said fluid to and discharging said fluid from said housing; and
   drive means including an electric motor disposed within said rotor and planetary gear transmission means operatively connected to said rotor and to said motor whereby said rotor is driven to cause said trochoidal movement of said edges along said surface and eccentric rotation of said rotor in said housing, said drive means having an eccentric shaft extending toward a lateral wall of said housing, and journaled for rotation relative thereto, said eccentric shaft being offset from a shaft of said motor, and defining an eccentric axis for said rotor at said lateral wall of said housing, and rotating contact means cooperating with said eccentric shaft at said lateral wall for energizing said electric motor.

2. The pump defined in claim 1 in a 1:2 ratio wherein said surface is a single-lobe trochoidal surface and said rotor has two opposite edges forming said seals, said planetary gear transmission means including planet gears journaled on respective planet shafts fixed to said rotor at diametrically opposite sides of an axis of rotation thereof on said eccentric.

3. The pump defined in claim 1 wherein said surface is a two-lobe trochoidal surface and said rotor has three angularly equispaced edges forming said seals, said planetary gear transmission means including three planet gears on respective shafts fixed to said rotor and angularly equispaced about an axis of rotation thereof on said eccentric.

4. The pump defined in claim 1 wherein said housing and said rotor form respective pump elements and said planetary gear transmission means includes at least one-stage speed-reducing planetary gearing having a sun gear forming a first member, a plurality of planet gears meshing with said sun gear and rotatable on respective shafts forming a second member and a further gear meshing with said planet gears and forming a third member of said gearing, one of said members being operatively connected to said shaft of said motor, another of said members being operatively connected to said motor and the remaining member being operatively connected to a pump element with respect to which said rotor is rotatable.

5. The pump defined in claim 4 wherein said motor has a casing forming said element.

6. The pump defined in claim 4 wherein said housing forms said element.

7. The pump defined in claim 1 wherein said motor has a casing and said rotor is journaled on said casing.

8. The pump defined in claim 7 wherein said casing forms said eccentric.

9. The pump defined in claim 1 wherein said planetary gear transmission means is disposed wholly within said rotor.

10. The pump defined in claim 9 wherein said motor is disposed on one axial side of said rotor and said planetary gear transmission means is disposed at the opposite axial side hereof and has a rotary member coaxial with said eccentric shaft and engaging an opposite lateral wall of said housing.

11. The pump defined in claim 9 wherein said planetary gear transmission means is disposed centrally in said rotor and is flanked by two such electric motors each of which has a respective eccentric shaft engaging a respective lateral wall of said housing and a respective motor shaft connected with said planetary gear transmission means.

12. The pump defined in claim 1 wherein a shaft coaxial with the axis of said eccentric shaft is formed with a bore, said pump further comprising a plug contactor in said bore for electrically connecting said motor with a source of electric current.

13. The pump defined in claim 1 wherein said ports are formed in said peripheral wall and, in a dead-point position of said rotor, said ports are disposed opposite said edges.

14. The pump defined in claim 1 wherein at least one of said ports is formed in a lateral wall of said housing and in a dead-point position of said rotor is disposed within flanks of said rotor so as to be blocked by said rotor.

15. The pump defined in claim 1 wherein at least one of said ports is formed in said walls and opens at said surface in an elongated pocket having control edges cooperating with said rotor to permit valveless operation of said pump.

16. The pump defined in claim 1 wherein said planetary gear transmission means includes a transmission disposed on an opposite side of said lateral wall from said electric motor.

17. The pump defined in claim 16, further comprising a speed reducer connected to said motor and disposed therewith within said rotor and connected to the gearing on said opposite side of said lateral wall.

18. The pump defined in claim 1 wherein said edges are formed with a circular curvature of a radius less than equidistant free center of said curvature to said surface whereby said seal is a gap seal having a constant spacing.

19. The pump defined in claim 1, provided with means for connecting it to the blood circulation of a patient to assist the patient's heart.

20. The pump defined in claim 1 provided with means for connecting same to the vena cavae, pulmonary veins, pulmonary arteries and aorta of a patient as an artificial heart.

* * * * *